(12) United States Patent
Balaraman et al.

(10) Patent No.: US 10,787,418 B1
(45) Date of Patent: Sep. 29, 2020

(54) PALLADIUM (II)-CATALYZED γC(SP³)-H ALKYNYLATION OF AMINES

(71) Applicant: Council of Scientific & Industrial Research, New Delhi (IN)

(72) Inventors: Ekambaram Balaraman, Maharashtra (IN); Vinod Gokulkrishna Landge, Maharashtra (IN); Akash Mondal, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/419,341

(22) Filed: May 22, 2019

(30) Foreign Application Priority Data

Apr. 3, 2019 (IN) .............................. 201911013443

(51) Int. Cl.
| | |
|---|---|
| *C07D 241/20* | (2006.01) |
| *C07D 213/127* | (2006.01) |
| *C07D 213/56* | (2006.01) |
| *C07D 221/04* | (2006.01) |
| *C07D 231/56* | (2006.01) |
| *C07D 471/04* | (2006.01) |
| *C07D 401/12* | (2006.01) |
| *B01J 31/04* | (2006.01) |
| *B01J 31/24* | (2006.01) |
| *C07D 231/44* | (2006.01) |

(52) U.S. Cl.
CPC .......... *C07D 213/127* (2013.01); *B01J 31/04* (2013.01); *B01J 31/2404* (2013.01); *C07D 213/56* (2013.01); *C07D 221/04* (2013.01); *C07D 231/44* (2013.01); *C07D 231/56* (2013.01); *C07D 241/20* (2013.01); *C07D 401/12* (2013.01); *C07D 471/04* (2013.01); *B01J 2231/32* (2013.01); *B01J 2531/824* (2013.01)

(58) Field of Classification Search
CPC ............. C07D 213/127; C07D 213/56; C07D 231/56; C07D 231/44; C07D 471/04; C07D 401/12; C07D 241/20; C07D 221/04; B01J 31/2404; B01J 31/04; B01J 2231/32; B01J 2531/824
USPC ....................................................... 544/406
See application file for complete search history.

(56) References Cited

PUBLICATIONS

Landge et al, Pd(II)-catalyzed gamma-C(sp3)-H alkynylation of amides, 2018, 54, 7483-7486 . . . (Year: 2018).*

* cited by examiner

*Primary Examiner* — Taylor V Oh
(74) *Attorney, Agent, or Firm* — Wood Herron & Evans LLP

(57) ABSTRACT

The present invention relates to a Palladium (II)-catalyzed C(sp³)-H alkynylation of amines using picolinamide as directing group. The developed alkynylation strategy is simple, efficient, and tolerant of various ring size including five to eight member cyclic, quaternary amines, and N-heterocyclic motifs.

8 Claims, 1 Drawing Sheet

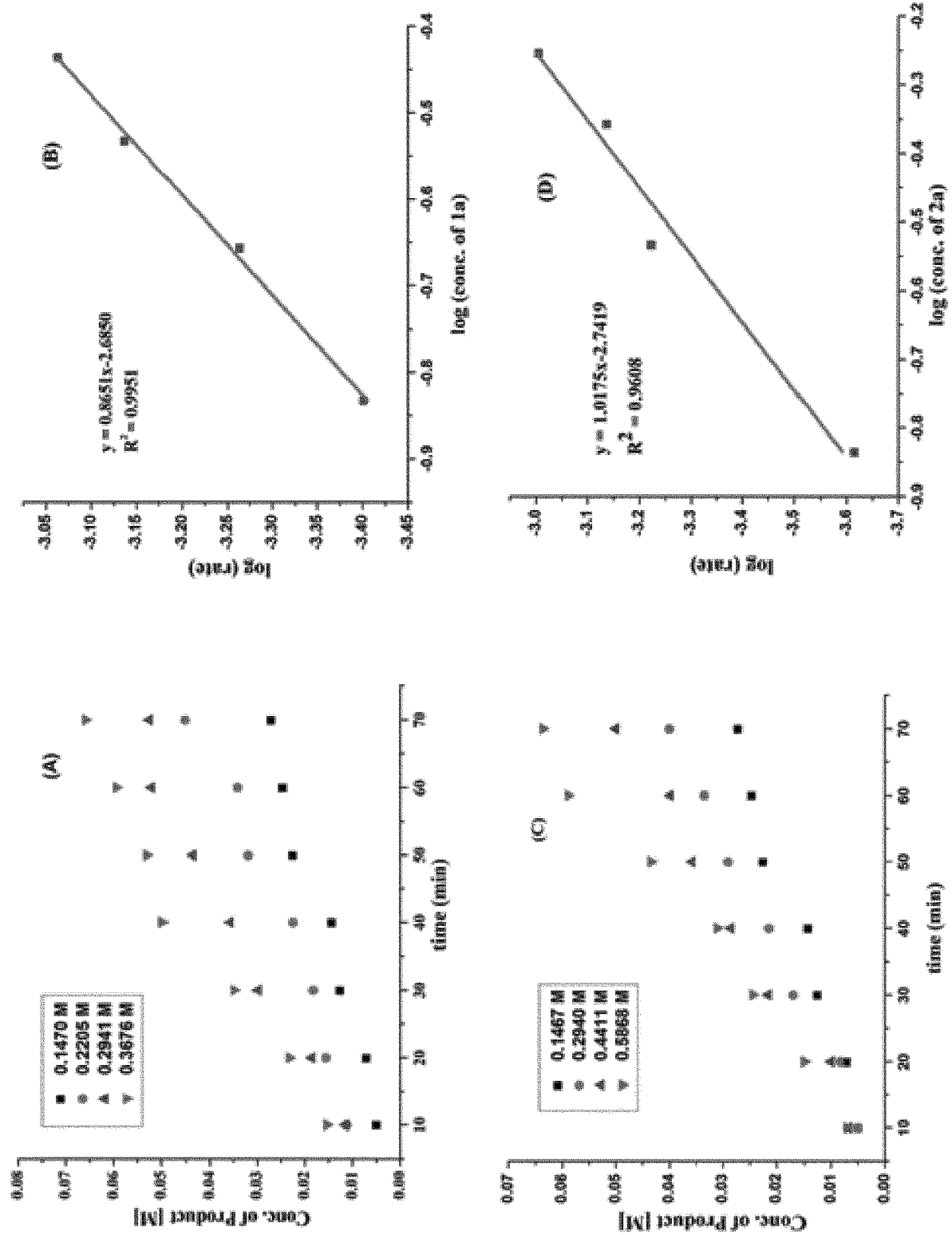

US 10,787,418 B1

PALLADIUM (II)-CATALYZED γC(SP³)-H ALKYNYLATION OF AMINES

FIELD OF THE INVENTION

The present invention relates to a process for Palladium (II)-catalyzed C(sp³)-H preferably γ C(sp³)-H alkynylation of amines using picolinamide as directing group.

BACKGROUND AND PRIOR ART OF THE INVENTION

The alkynes are essential functional group in many cross-coupling, metathesis and cycloaddition reactions. As a result, it has a prominent role in drug discovery, material science, and the chemical industry. The "inverse Sonogashira coupling" involving the direct approach for sp²-sp C—C cross-coupling of inert aryl C—H bonds with easily accessible alkynyl halides, is very attractive and highly desirable in organic synthesis. Thus, metal-catalyzed C—H alkynylation would offer an alternative method to install alkyne group on C (sp²)-H and C(sp³)-H bond with high efficiency. However, metal-catalyzed sp³-sp bond formation is a challenge and remains extremely rare. The amines have to constitute important synthetic precursors and are ubiquitous in agrochemical, peptide, pharmaceutical, and functional materials.

Article titled, "Well-Defined Palladium-(II) Complexes for Ligand-Enabled C(sp3)-Alkynylation" by Ekambaram Balaraman et al. published in *Dalton Transactions*, 2015, 44, 15382-15386 reports ligand-enabled C(sp³)-H alkynylation of 8-methylquinoline. The reaction is catalysed by the well defined Pd(II)-complexes. The present C(sp³)-alkynylation has a broad substrate scope as well as functional group tolerance and proceed efficiently under mild conditions.

Article titled, "Nickel-catalyzed direct alkynylation of C(sp²)-H bonds of amides: an "inverse Sonogashira strategy" to ortho-alkynylbenzoic acids" by Ekambaram Balaraman et al. published in *Catalysis Science and Technology*, 2016, 6, 1946 reports Nickel-catalyzed direct alkynylation of C(sp²)-H bonds of amides using commercially available, inexpensive 8-aminoquinoline as a removable bidentate directing group. The present ortho-alkynylation has a broad substrate scope, functional group tolerance and high regio-control, and can be scaled up. The efficiency and selectivity of this strategy provide sustainable routes to a diverse array of orthoalkynylbenzoic acids under Ni(II)-catalyzed conditions.

Article titled, "Cobalt-Catalyzed Bis-alkynylation of Amides via Double C—H Bond Activation" by Ekambaram Balaraman et al. published in *Organic Letters*, 2016, 18, 812-815 reports the first example of cobalt-catalyzed selective bis-alkynylation of amides via double C—H bond activation with the directing assistance of a removable bidentate auxiliary. The developed alkynylation strategy is simple, efficient, and tolerant of various functional groups including ether, amine, halides, and heterocyclic motifs. The reaction can be scaled up under mild conditions.

Article titled, "Palladium-Catalyzed Direct Ethynylation of C(sp³)-H Bonds in Aliphatic Carboxylic Acid Derivatives" by Yusuke Ano et al. published in *Journal of American Chemical Society*, 2011, 133, 12984-12986 reports The first catalytic alkynylation of unactivated C(sp³)-H bonds has been accomplished. The method allows for the straightforward introduction of an ethynyl group into aliphatic acid derivatives under palladium catalysis. This new reaction can be applied to the rapid elaboration of complex aliphatic acids, for example, via azide/alkyne cycloaddition.

To discover a new catalytic system which minimizes the synthetic steps, for selective organic transformations is important for chemical industries. Recently, transition-metal catalyzed C—H bond activation attains a huge interest for the development of various synthetic transformations in a sustainable manner. Alkynylation of amines is the most significant tool to elongation of amines. However, the reaction proceeds under various size of ring which is found in the most of the drug molecules contain amines. Till a date there is no report on synthesized of alkynylated amines via C—H bond activation. However in case of amino-acid prior art achieved the C—H alkynylation at beta position but present case inventor observed alkynylaton at the gamma position of amines. So by considering all these points present inventors provides a highly selective palladium (11)-catalyzed γ C(sp³)-H alkynylation of amines.

OBJECTIVES OF THE INVENTION

The main objective of the present invention is to provide a process for Palladium (II)-catalyzed C(sp³)-H preferably γ C(sp³)-H alkynylation of amines using picolinamide as directing group.

SUMMARY OF THE INVENTION

The present invention provides a process for Palladium (II)-catalyzed C(sp³)-H preferably γ C(sp³)-H alkynylation of amines using picolinamide as directing group comprises heating the reaction mixture of amine, haloalkyne, palladium catalyst, oxidant and solvent for time period is in the range of 18 to 20 hours at temperature is selected in the range of 130° C. to 140° C. to afford alkynylated product.

ABBREVIATION

Pd(OAc)₂: Palladium(II) acetate
Pd(OPiv)₂: 2,2-Dimethylpropanoic acid palladium (II) salt
Pd(PPh₃)₄: Tetrakis(triphenylphosphine)palladium(0)
Pd(PPh₃)₂Cl₂: Bis(triphenylphosphine)palladium(II) dichloride
Pd(dba)₄: Tris(dibenzylideneacetone)dipalladium(0)
Pd(OTf)₂: Palladium(II) trifluoroacetat
Pd(CH₃CN)₄BF₄: Tetrakis(acetonitrile)palladium(II) tetrafluoroborate
PdCl₂: Palladium(II) chloride
Pd(TFA)₂: Palladium(II) trifluoroacetate

BRIEF DESCRIPTION OF THE DRAWINGS

FIG. 1: Kinetics study. (A) The graph of product concentration vs. time with increasing concentration of 1a. (B) Graph of log (rate) vs. log (conc. of 1a). (C) Graph of product concentration vs. time with increasing concentration of 2. (D) Graph of log (rate) vs. log (conc. of 2).

DETAILED DESCRIPTION OF THE INVENTION

The invention will now be described in detail in connection with certain preferred and optional embodiments, so that various aspects thereof may be more fully understood and appreciated.

The present invention provides a Palladium (II)-catalyzed C(sp³)-H preferably γ C(sp³)-H alkynylation of amines using picolinamide as directing group comprises heating the reaction mixture of amide, haloalkyne, palladium catalyst, oxidant and solvent for 18 to 20 hours at temperature is in the range of 130° C. to 140° C. to afford alkynylated product.

Amides are synthesized by using corresponding acids such as 6-methyl picolic acid, 3 methyl picolinic acid, pyrazinic acid, quinol quinoline-2-carboxylic acid, isoquinoline-1-carboxylic acid, 1H-indazole-3-carboxylic acid, pyrazine-2-carboxylic acid.

The amine is selected from the group consisting of cyclohexanamine, 4-methylcyclohexanamine, 4-butylcyclohexanamine, cyclopentanamine, cycloheptanamine, cyclooctanamine, methyl 1-aminocyclopentanecarboxylate, ethyl 1-aminocyclopentanecarboxylate, 5-methylhexan-2-amine, nonan-2-amine The amide is selected from the group consisting of N-cyclohexylpicolinamide, N-(4-methylcyclohexyl)picolinamide, N-(4-butylcyclohexyl)picolinamide, N-cyclopentylpicolinamide, N-cycloheptylpicolinamide, N-cyclooctylpicolinamide methyl 1-(picolinamido) cyclopentanecarboxylate, ethyl 1-(picolinamido) cyclopentanecarboxylate, tert-butyl 3-(picolinamido) piperidine-1-carboxylate, N-(5-methylhexan-2-yl)picolinamide, N-(octan-2-yl)picolinamide, N-cyclohexyl-6-methylpicolinamide, N-cyclohexyl-3-methylpicolinamide, N-cyclohexylpyrazine-2-carboxamide, N-cyclohexyl-5-methylpyrazine-2-carboxamide, N-cyclohexylquinoline-2-carboxamide, N-cyclohexylisoquinoline-1-carboxamide, N-cyclohexyl-1-methyl-1H-indazole-3-carboxamide.

The haloalkyne is selected from the group consisting of (bromoethynyl)triisopropylsilane, (bromoethynyl) (tert-butyl)dimethylsilane, tert-butyl(iodoethynyl)dimethylsilane, (bromoethynyl)dimethyl (phenyl)silane or (bromoethynyl) bezene.

The solvent is selected from the group consisting of toluene, trifluorotoluene, decane, octane, mesitylene, dioxane, t-amyl alcohol, dicholoro methane or dicholoro ethane.

The palladium catalyst is selected from the group consisting of $Pd(OAc)_2$, $Pd(OPiv)_2$, $Pd(PPh_3)_4$, $Pd(PPh_3)_2Cl_2$, $Pd(dba)_4$, $Pd(OTf)_2$, $Pd(CH_3CN)_4BF_4$, $PdCl_2$ or $Pd(TFA)_2$.

The oxidant is selected from the group consisting of silver carbonate, silver acetate, silver benzoate, silver triflate or silver nitrate.

The alkynylated product is selected from the group consisting of
  i. N-(2-((triisopropylsilyl)ethynyl)cyclohexyl)picolinamide (3a);
  ii. N-(4-methyl-2-((triisopropylsilyl)ethynyl)cyclohexyl) picolinamide (3b);
  iii. N-(4-butyl-2-((triisopropylsilyl)ethynyl)cyclohexyl) picolinamide (3c);
  iv. N-(2-((triisopropylsilyl)ethynyl)cyclopentyl)picolinamide (3d);
  v. N-(2-((triisopropylsilyl)ethynyl)cycloheptyl)picolinamide (3e);
  vi. N-(2-((triisopropylsilyl)ethynyl)cyclooctyl)picolinamide (3f);
  vii. Methyl 1-(picolinamido)-3-((triisopropylsilyl)ethynyl)cyclopentanecarboxylate (3g);
  viii. Ethyl 1-(picolinamido)-3-((triisopropylsilyl)ethynyl) cyclopentanecarboxylate (3h);
  ix. N-(2-((tert-butyldimethyl silyl)ethynyl)cyclohexyl)picolinamide (3i);
  x. (3R)-tert-butyl 3-(picolinamido)-5-((triisopropylsilyl) ethynyl)piperidine-1-carboxylate (3j);
  xi. N-(4-((triisopropylsilyl)ethynyl)heptan-2-yl)picolinamide (3k);
  xii. N-(7-methyl-1-(triisopropylsilyl)oct-1-yn-4-yl)picolinamide (3l);
  xiii. 6-methyl-N-(2-((triisopropylsilyl)ethynyl)cyclohexyl)picolinamide (3m);
  xiv. 3-methyl-N-(2-((triisopropylsilyl)ethynyl)cyclohexyl)picolinamide (3n);
  xv. N-(2-((triisopropylsilyl)ethynyl)cyclohexyl)pyrazine-2-carboxamide (3o);
  xvi. 5-methyl-N-(2-((triisopropylsilyl)ethynyl)cyclohexyl)pyrazine-2-carboxamide (3p);
  xvii. N-(2-((triisopropylsilyl)ethynyl)cyclohexyl)quinoline-2-carboxamide (3 q);
  xviii. N-(2-((triisopropylsilyl)ethynyl)cyclohexyl)isoquinoline-1-carboxamide (3r) or
  xix. 1-methyl-N-(2-((triisopropylsilyl)ethynyl)cyclohexyl)-1H-indazole-3-carb oxamide (3 s)

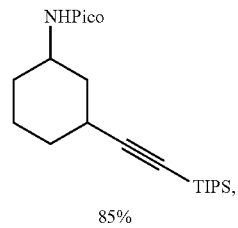

3a

85%

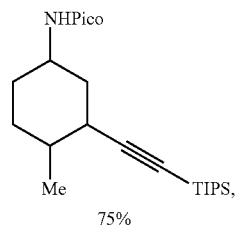

3b

75%

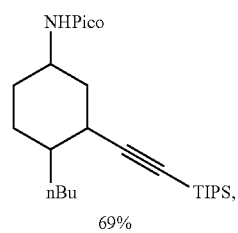

3c

69%

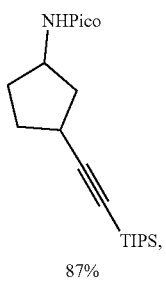

3d

87%

-continued
| | |
|---|---|
| 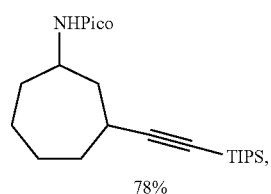 78% | 3e |
| 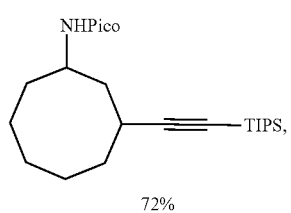 72% | 3f |
| 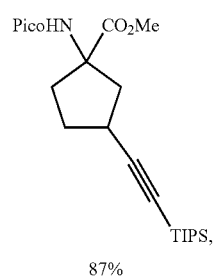 87% | 3g |
| 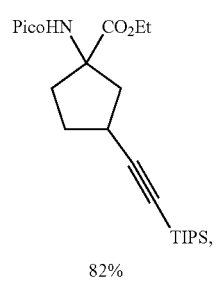 82% | 3h |
| 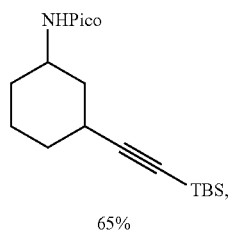 65% | 3i |
| 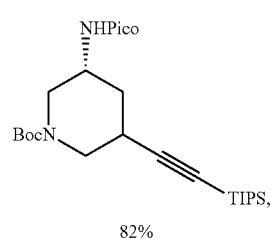 82% | 3j |
-continued
| | |
|---|---|
| 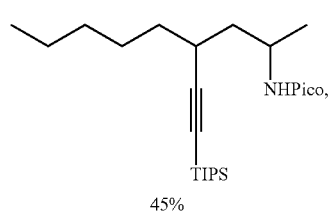 45% | 3k |
| 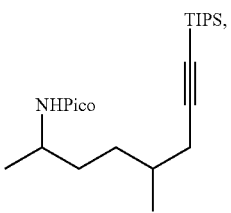 30% | 3l |
| 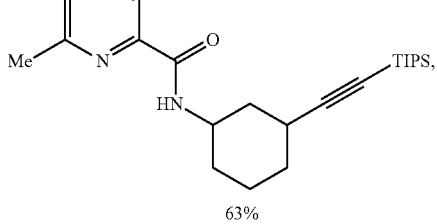 63% | 3m |
| 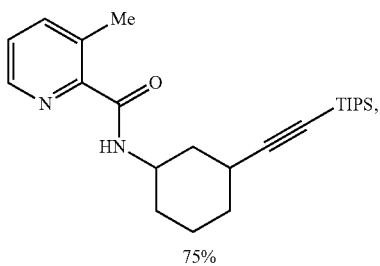 75% | 3n |
| 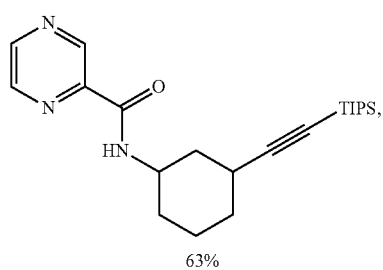 63% | 3o |
| 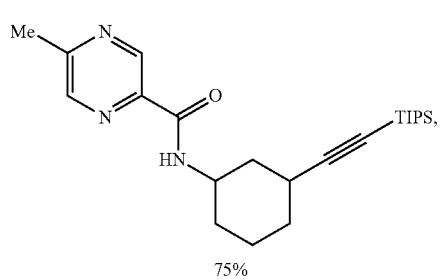 75% | 3p |

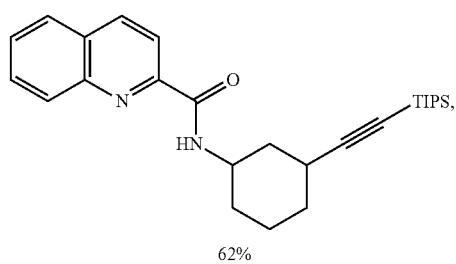

3q, 62%

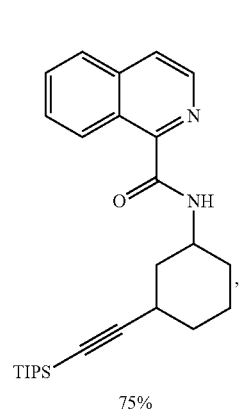

3r, 75%

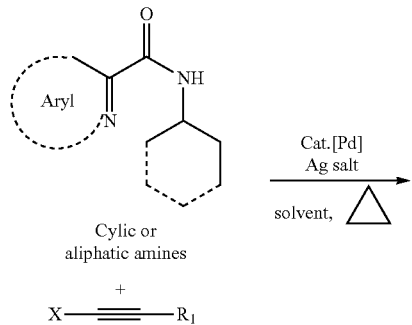

3s, 45%

The Palladium (II)-catalyzed C (sp³)-H alkynylation of amines using picolinamide as directing group is shown as below:

Scheme 1

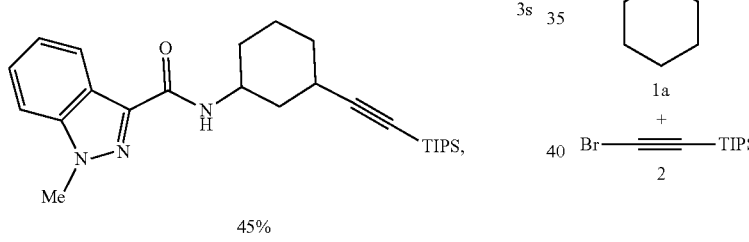

Cylic or aliphatic amines

+

X≡≡R₁

Cat.[Pd] Ag salt
solvent, △

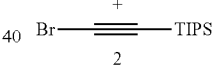
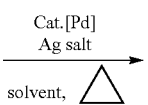
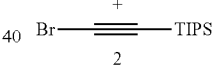
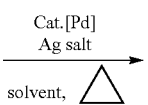

Wherein R¹ is selected from the group consisting of triisopropylsilyl, tbutyl dimethyl silyl, triphenyl silyl or phenyl dimethylsilyl.

Inventor studied said reaction in different reaction conditions. Table 1 shows the study of different reaction conditions.

Scheme 2

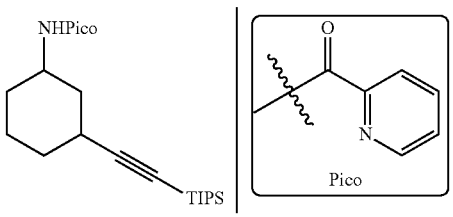

TABLE 1

Study of different reaction conditions.

| Entry | Reaction conditions | Yield of 3a (%)[b] | Recovered 1a (%)[b] |
|---|---|---|---|
| 1 | Pd(PPh$_3$)$_2$Cl$_2$ used as [Pd] source | 15% | 78% |
| 2 | Pd(TFA)$_2$ used as [Pd] source | No reaction | 98% |
| 3 | standard conditions | 85% | 8% |
| 4 | Pd(dba)$_3$ used as [Pd] source | 20% | 71% |
| 5 | Pd(CH$_3$CN)$_4$BF$_4$ used as [Pd] source | trace | 97% |
| 6 | PdCl$_2$ used as [Pd] source | trace | 98% |
| 7 | Pd(acac)$_2$ used as [Pd] source | trace | 97% |
| 8 | at 100° C. | 75% | 21% |
| 9 | without [Pd] cat | No reaction | 95% |
| 10 | without AgOAc | trace | 92% |
| 11 | (bromoethynyl)benzene instead of 2 | No reaction | 99% |
| 12 | Ag$_2$CO$_3$ instead of AgOAc | 75% | 10% |
| 13 | PhCO$_2$Ag instead of AgOAc | 35% | 58% |
| 14 | HFIP used as solvent | trace | 98% |
| 15 | CF$_3$CH$_2$OH used as solvent | trace | 97% |

Reaction conditions: 1a (0.1 mmol), 2 (0.12 mmol), Pd(OAc)$_2$ (0.01 mmol), AgOAc (0.20 mmol) and toluene (1 mL) heated at 130° C. (bath temperature) for 18 h under argon atm. [b]Isolated yields.

Other solvents such as DMA, DCE, HFIP, and CF$_3$CH$_2$OH are found to be ineffective, and no (or trace) alkynylated product 3a was observed under optimal conditions.

In an embodiment, the present invention provides site selective Palladium (II)-catalyzed C (sp$^3$)-H alkynylation of amines. Scheme 2 shows site-selective alkynylation process.

Scheme 3

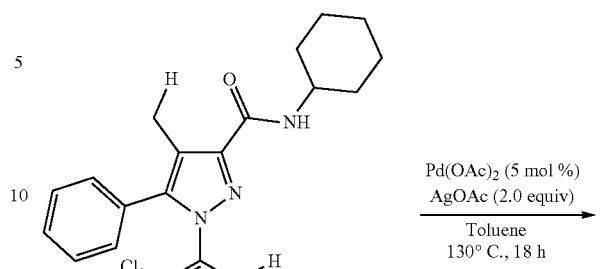

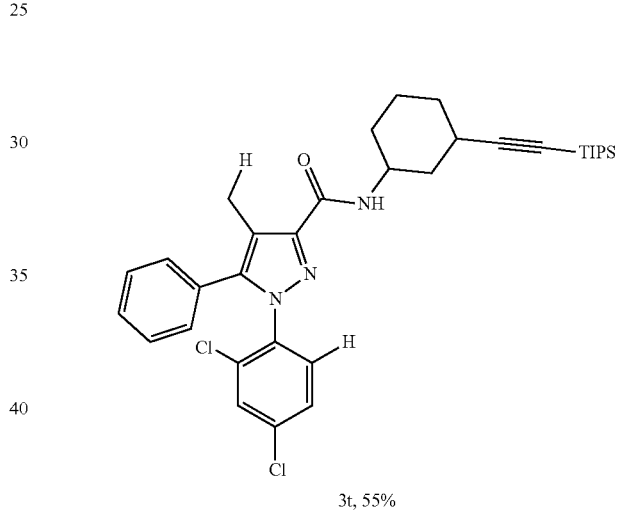

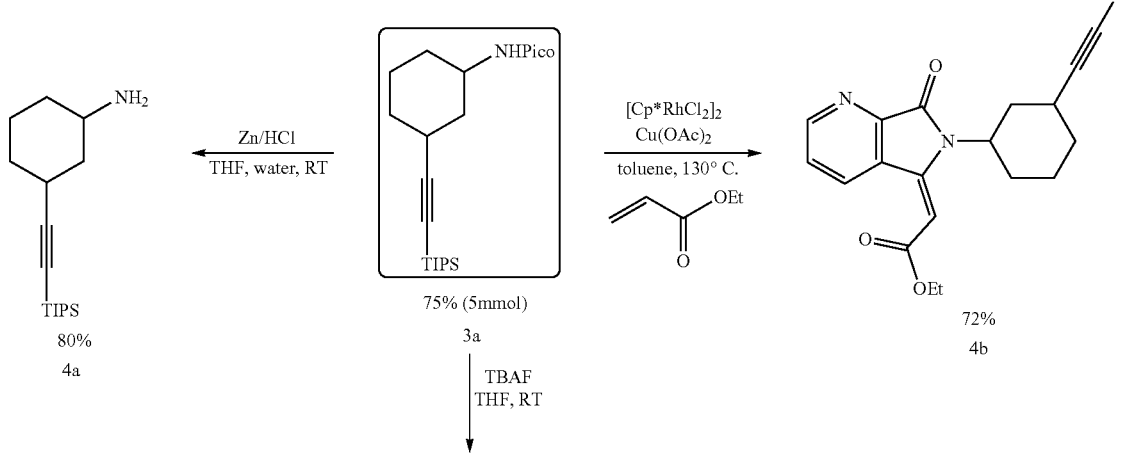

-continued

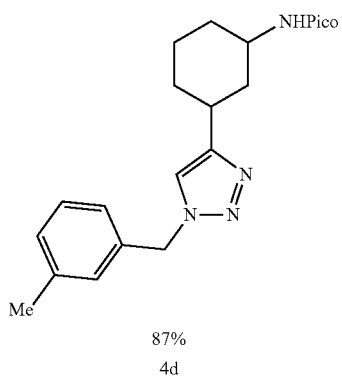

87%
4d

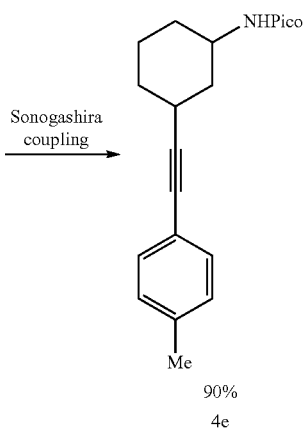

99%
4c cat. CuI
3-Me-BnN₃
———————→
DMF, 60° C.

Sonogashira
coupling
———————→

90%
4e

The kinetic studies are carried out to determine the order of the reaction in the palladium catalyzed γ-alkynylation of amide 1a with 2 by using the initial rate approximation (FIG. 1). The data shows that the increase in the concentration of 1a enhances the rate of the reaction with a slope of 0.86 obtained from the plot of log(rate) vs. log(conc. of 1a), indicating a fractional order alkynylation reaction. Similarly, upon increasing the concentration of 2, the rate of the reaction increased, and a slope of 1.01 is obtained from the plot of log(rate) vs. log(conc. of 2). Thus, the rate of the reaction depends on both the substrates.

EXAMPLES

Following examples are given by way of illustration therefore should not be construed to limit the scope of the invention.

Example 1: General Procedure for the Palladium-Catalyzed C(sp$^3$)-Alkynylation of Amine To an oven-dried 10 mL screw-capped vial, picolinamide (0.25 mmol), (bromoethynyl)triisopropylsilane 2 (0.27 mmol), Pd(OAc)$_2$ (10 mol %), Ag$_2$CO$_3$ (2 equiv), and toluene (1 mL) were added under a gentle stream of argon. The mixture was stirred for 18 hrs at 130° C. (bath temperature) followed by cooling to 28° C. The mixture was filtered through a celite pad with several washings (3×3 mL dichloromethane) and concentrated in vacuo. The residue was purified by column chromatography on silica gel (eluent: pet ether/EtOAc) to afford the desired alkynylated product 3.

Example 2: Synthesis of 4a (Removal of Directing Group)

To a suspension of the starting 3a (0.15 mmol, 1.0 equiv) in THF (1.5 mL) was added water (1.5 mL) followed by 12M HCl (0.37 mL) and the mixture was stirred for 5 minutes at 28° C. Zinc dust (145 mg, 2.24 mmol, 15 equiv) was then added in three portions and the mixture was stirred at 28° C. After 1.5 h, the reaction was filtered through a celite plug. The filtrate was transferred to a separating funnel with 2M NaOH (50 mL) and extracted twice with DCM (2×50 mL). The combined organic phase was dried over Na$_2$SO$_4$ and concentrated in vacuo. The residue was purified by column chromatography on silica gel (eluent: MeOH/DCM) to afford the desired product 4a (33 mg, 80%, yellow liquid).

Example 3: Synthesis of 4b

To an oven-dried 10 mL screw-capped vial, amide 3a (38 mg, 0.1 mmol), ethyl acrylate (20 mg, 0.15 mmol), [Cp*RhCl$_2$]$_2$ (5 mol %), Cu(OAc)$_2$ (2 equiv), and toluene (1 mL) were added under a gentle stream of argon. The mixture was stirred for 24 hrs at 130° C. (bath temperature) followed by cooling to 28° C. The mixture was filtered through a celite pad with several washings (3×3 mL dichloromethane) and concentrated in vacuo. The residue was purified by column chromatography on silica gel (eluent: pet ether/EtOAc) to afford the desired product 4b (34 mg, 72%, yellow liquid).

Example 4: Synthesis of 4c

The corresponding compound 3a (500 mg, 1.3 mmol), was dissolved in THF and 1.0 M TBAF in THF (1.5 equiv) was then added at 0° C. with constant stirring. The reaction progress was monitored by TLC. The mixture was diluted with water extracted with EtOAc, dried over anhydrous Na$_2$SO$_4$, filtered and evaporated in vacuo. The obtained crude product was purified by column chromatography to afford the desired terminal alkyne product 4c (294 mg, 99%, yellow liquid).

Example 5: Synthesis of 4d

Under argon atm 4c (34 mg. 0.15 mmol, 1.0 equiv), CuI (10 mol %) and 3-methyl benzyl azide (20 mg, 0.15 mmol, 1.0 equiv) were dissolved in DMF (1 mL) and stirred at 60° C. for 16 hrs. After completion of the reaction saturated aq. NH$_4$Cl solution (5 mL) was added and the mixture was extracted with dichloromethane (3×5 mL) and dried over anhydrous Na$_2$SO$_4$. After complete evaporation of the solvent, the obtained crude product was purified by column chromatography to afford 4d (49 mg, 87%, yellow solid).

Example 6: Synthesis of 4e

Under argon atm 4c (prepared by the above mentioned procedure) (34 mg, 0.15 mmol), iodobenzene (39 mg, 0.18 mmol), PdCl$_2$ (5 mol %), CuI (2.5 mol %), Et$_3$N (1 mL)

were charged to a 25 mL Schlenk tube. The reaction mixture was stirred at 50° C. for 12 hrs. The mixture was filter through celite and concentrated in vacuo. The obtained crude product was purified by column chromatography to afford 4e (43 mg, 90%, white solid).

Example 7: Characterization Data

A. N-cyclohexyl-1-(2,4-dichlorophenyl)-4-methyl-5-phenyl-1H-pyrazole-3-carboxamide (1t)

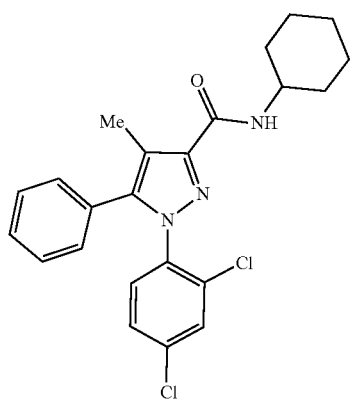 [SMILES: Cc1c(C(=O)NC2CCCCC2)nn(-c2ccc(Cl)cc2Cl)c1-c1ccccc1]

$^1$H NMR (500 MHz, CHLOROFORM-d) δ ppm 7.41 (d, J=1.1 Hz, 1H), 7.34-7.22 (m, 5H), 7.13 (td, J=2.8, 3.9 Hz, 2H), 6.85 (d, J=8.0 Hz, 1H), 4.02-3.87 (m, 1H), 2.42-2.32 (m, 3H), 2.10-1.96 (m, 2H), 1.76 (td, J=3.4, 13.4 Hz, 2H), 1.70-1.57 (m, 1H), 1.50-1.36 (m, 2H), 1.32-1.19 (m, 4H). $^{13}$C NMR (126 MHz, CHLOROFORM-d) δ ppm 162.0, 145.2, 144.2, 136.3, 135.7, 133.1, 130.7, 130.2, 129.6, 128.9, 128.6, 128.5, 127.7, 117.5, 47.9, 33.2, 25.6, 25.1, 9.5 HRMS (EI): m/z Calcd for [M+H] $C_{23}H_{24}ON_3Cl_2$: 428.1291; Found: 428.1289.

B. N-(2-((triisopropylsilyl)ethynyl)cyclohexyl)picolinamide (3a)

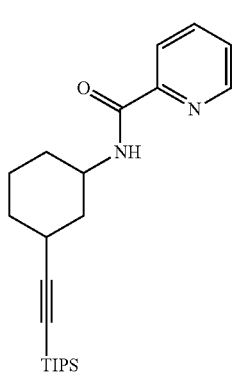

82 mg, 85% isolated yield. $R_f$=0.32 (hexane/EtOAc=9/1). Yellow liquid. $^1$H NMR (500 MHz, CHLOROFORM-d) δ ppm 8.54 (d, J=4.2 Hz, 1H), 8.20 (d, J=8.0 Hz, 1H), 7.93 (d, J=8.0 Hz, 1H), 7.84 (dt, J=1.7, 7.7 Hz, 1H), 7.47-7.37 (m, 1H), 4.06-3.86 (m, 1H), 2.54-2.42 (m, 1H), 2.37 (d, J=12.6 Hz, 1H), 2.10-1.93 (m, 2H), 1.84 (td, J=3.1, 13.5 Hz, 1H), 1.46-1.22 (m, 4H), 1.04 (s, 21H). $^{13}$C NMR (126 MHz, CHLOROFORM-d) δ ppm 163.3, 150.0, 147.9, 137.3, 126.1, 122.3, 112.1, 79.5, 77.3, 76.7, 47.6, 39.4, 32.5, 32.3, 29.8, 24.4, 18.6, 11.2. HRMS (EI): m/z Calcd for [M+H] $C_{20}H_{31}N_2OSi$: 343.2200; Found: 343.2200.

C. N-(4-methyl-2-((triisopropylsilyl)ethynyl)cyclohexyl)picolinamide (3b)

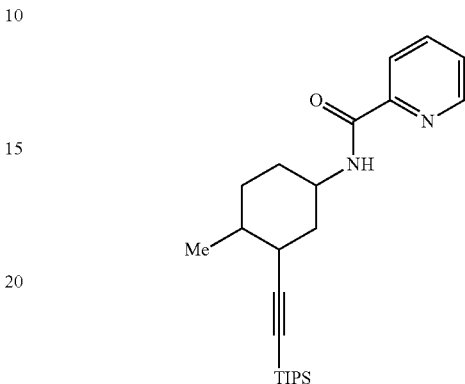

75 mg, 75% isolated yield. $R_f$=0.32 (hexane/EtOAc=9/1). Yellow liquid. $^1$H NMR (500 MHz, CHLOROFORM-d) δ ppm 8.55-8.49 (m, 1H), 8.19 (d, J=8.0 Hz, 1H), 7.88-7.78 (m, 1H), 7.45-7.33 (m, 1H), 2.81-2.70 (m, 1H), 2.20-2.02 (m, 2H), 2.02-1.96 (m, 1H), 1.86-1.64 (m, 3H), 1.61 (d, J=9.2 Hz, 2H), 1.13-1.09 (m, 4H), 1.08-0.98 (m, 22H). $^{13}$C NMR (126 MHz, CHLOROFORM-d) δ ppm 163.5, 163.4, 150.1, 150.0, 147.9, 137.3, 137.2, 126.0, 126.0, 122.3, 122.2, 111.2, 110.8, 81.6, 80.6, 47.7, 47.1, 39.4, 37.2, 37.2, 33.5, 33.3, 33.2, 32.7, 31.4, 29.3, 27.3, 20.4, 18.6, 11.2. HRMS (EI): m/z Calcd for [M+H]$C_{24}H_{39}N_2OSi$: 399.2826; Found: 399.2827.

D. N-(4-butyl-2-((triisopropylsilyl)ethynyl)cyclohexyl)picolinamide (3c)

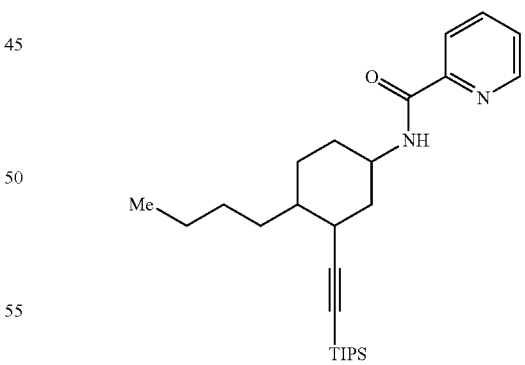

76 mg, 69% isolated yield. $R_f$=0.32 (hexane/EtOAc=9/1). Yellow liquid. $^1$H NMR (500 MHz, CHLOROFORM-d) δ ppm 8.53 (dd, J=4.6, 9.2 Hz, 1H), 8.20 (dd, J=3.4, 7.6 Hz, 1H), 8.00-7.77 (m, 2H), 7.50-7.32 (m, 1H), 3.93 (dtd, J=4.2, 7.9, 12.0 Hz, 1H), 2.40 (dd, J=2.3, 12.6 Hz, 1H), 2.23 (d, J=2.3 Hz, 1H), 2.14-1.96 (m, 1H), 1.96-1.85 (m, 1H), 1.80-1.71 (m, 1H), 1.71-1.56 (m, 2H), 1.54-1.39 (m, 2H), 1.39-1.17 (m, 8H), 1.14-0.96 (m, 23H), 0.96-0.84 (m, 3H). $^{13}$C NMR (126 MHz, CHLOROFORM-d) δ ppm 163.4, 150.0, 147.9, 137.3, 137.2, 126.0, 125.9, 122.3, 122.2, 111.3, 80.8, 47.7, 41.9, 39.7, 35.8, 34.1, 34.0, 32.7, 32.1, 32.0, 29.9, 27.2, 26.1, 22.6, 22.5, 18.6, 14.1, 11.3, 11.2. HRMS (EI): m/z Calcd for [M+H] $C_{24}H_{39}N_2OSi$: 441.3296; Found: 441.3293.

E. N-(2-((triisopropylsilyl)ethynyl)cyclopentyl)picolinamide (3d)

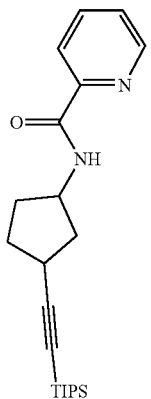

80 mg, 87% isolated yield. $R_f$=0.32 (hexane/EtOAc=9/1). Yellow liquid. $^1$H NMR (500 MHz, CHLOROFORM-d) δ ppm 8.52 (d, J=4.6 Hz, 1H), 8.27-8.05 (m, 2H), 7.84 (dt, J=1.5, 7.6 Hz, 1H), 7.41 (dd, J=5.0, 6.5 Hz, 1H), 4.50 (d, J=7.2 Hz, 1H), 2.87 (t, J=7.2 Hz, 1H), 2.55-2.37 (m, 1H), 2.16 (dd, J=5.5, 7.4 Hz, 1H), 2.07-1.97 (m, 1H), 1.97-1.86 (m, 1H), 1.86-1.65 (m, 3H), 1.09-1.00 (m, 22H). $^{13}$C NMR (126 MHz, CHLOROFORM-d) δ ppm 163.8, 149.9, 147.9, 137.2, 126.0, 122.1, 112.7, 80.3, 50.1, 41.1, 32.5, 32.5, 29.7, 18.7, 18.6, 11.2. HRMS (EI): m/z Calcd for [M+H] $C_{22}H_{35}N_2OSi$: 371.2513; Found: 371.2516.

F. N-(2-((triisopropylsilyl)ethynyl)cycloheptyl)picolinamide (3e)

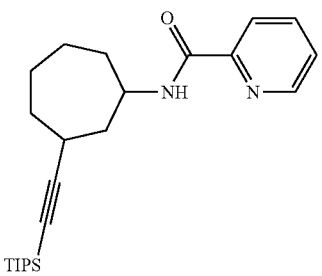

78 mg, 78% isolated yield. $R_f$=0.32 (hexane/EtOAc=9/1). Yellow liquid. $^1$H NMR (500 MHz, CHLOROFORM-d) δ ppm 8.52 (d, J=4.2 Hz, 1H), 8.19 (d, J=8.0 Hz, 1H), 8.14 (d, J=8.0 Hz, 1H), 7.83 (dt, J=1.5, 7.8 Hz, 1H), 7.41 (dd, J=4.8, 6.7 Hz, 1H), 4.22 (td, J=4.6, 9.2 Hz, 1H), 2.83-2.71 (m, 1H), 2.28 (td, J=3.4, 14.1 Hz, 1H), 2.06 (ddd, J=3.8, 6.9, 13.7 Hz, 1H), 1.95-1.85 (m, 2H), 1.84-1.64 (m, 5H), 1.59-1.45 (m, 1H), 1.14-0.96 (m, 21H). $^{13}$C NMR (126 MHz, CHLOROFORM-d) δ ppm 162.9, 150.1, 147.9, 137.2, 126.0, 122.2, 113.1, 80.6, 77.3, 76.7, 48.9, 41.4, 35.5, 34.9, 29.4, 25.8, 24.3, 18.6, 11.2 HRMS (EI): m/z Calcd for [M+H] $C_{24}H_{39}N_2OSi$: 399.2826; Found: 399.2827.

G. N-(2-((triisopropylsilyl)ethynyl)cyclooctyl)picolinamide (3f)

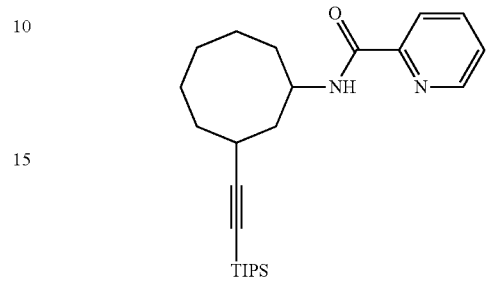

74 mg, 72% isolated yield. $R_f$=0.32 (hexane/EtOAc=9/1). Yellow liquid. $^1$H NMR (400 MHz, CHLOROFORM-d) δ ppm 8.54 (d, J=4.3 Hz, 1H), 8.20 (d, J=7.9 Hz, 1H), 8.08 (d, J=7.9 Hz, 1H), 7.84 (t, J=7.0 Hz, 1H), 7.42 (dd, J=4.9, 7.3 Hz, 1H), 4.19 (dd, J=4.3, 7.9 Hz, 1H), 2.84 (dd, J=4.0, 7.0 Hz, 1H), 2.22-2.09 (m, 1H), 2.06-1.92 (m, 3H), 1.92-1.65 (m, 5H), 1.61 (br. s., 5H), 1.10-0.97 (m, 22H). $^{13}$C NMR (101 MHz, CHLOROFORM-d) δ ppm 162.9, 150.2, 148.0, 137.3, 126.0, 122.2, 113.4, 79.9, 48.3, 39.3, 33.8, 31.9, 30.2, 26.8, 23.4, 22.5, 18.6, 11.2. HRMS (EI): m/z Calcd for [M+H] $C_{25}H_{41}N_2OSi$: 413.1983; Found: 413.2985.

H. Methyl 1-(picolinamido)-3-((triisopropylsilyl)ethynyl)cyclopentanecarboxylate (3g)

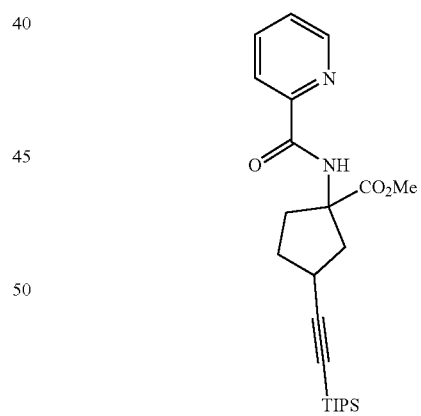

93 mg, 87% isolated yield. $R_f$=0.32 (hexane/EtOAc=9/1). Yellow liquid. $^1$H NMR (500 MHz, CHLOROFORM-d) δ ppm 8.55 (brs., 1H), 8.51 (brs., 1H), 8.15 (d, J=7.2 Hz, 1H), 7.84 (brs., 1H), 7.44 (brs., 1H), 3.74 (brs., 3H), 3.08 (brs., 1H), 2.85-2.76 (m, 1H), 2.51-2.39 (m, 1H), 2.35-2.24 (m, 1H), 2.24-2.14 (m, 2H), 2.02 (d, J=8.0 Hz, 1H), 1.00 (br. s., 21H). $^{13}$C NMR (126 MHz, CHLOROFORM-d) δ ppm 174.0, 164.1, 149.5, 148.0, 137.3, 126.3, 122.1, 111.4, 80.7, 65.1, 52.7, 44.9, 37.2, 33.1, 30.5, 18.6, 11.2. HRMS (EI): m/z Calcd for [M+H] $C_{24}H_{37}N_2O_3Si$: 429.2573; Found: 429.2546.

I. Ethyl 1-(picolinamido)-3-((triisopropylsilyl)ethynyl)cyclopentanecarboxylate (3h)

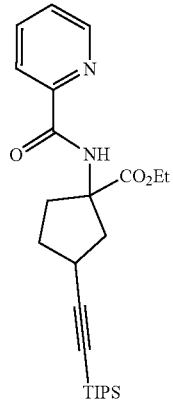

91 mg, 82% isolated yield. $R_f$=0.32 (hexane/EtOAc=9/1). Yellow liquid. $^1$H NMR (500 MHz, CHLOROFORM-d) δ ppm 8.65-8.47 (m, 2H), 8.15 (d, J=8.0 Hz, 1H), 7.84 (dt, J=1.5, 7.6 Hz, 1H), 7.43 (dd, J=5.0, 6.9 Hz, 1H), 4.21 (q, J=7.1 Hz, 2H), 3.08 (t, J=7.6 Hz, 1H), 2.80 (dd, J=8.4, 13.7 Hz, 1H), 2.50-2.36 (m, 1H), 2.34-2.26 (m, 1H), 2.26-2.13 (m, 2H), 2.02 (dd, J=8.0, 12.6 Hz, 1H), 1.24 (t, J=7.1 Hz, 4H), 1.08-0.89 (m, 21H). $^{13}$C NMR (126 MHz, CHLOROFORM-d) δ ppm 173.4, 164.0, 149.6, 148.0, 137.2, 126.2, 122.0, 111.5, 80.7, 65.1, 61.5, 44.8, 37.1, 33.2, 30.6, 18.6, 14.1, 11.2. HRMS (EI): m/z Calcd for [M+H] $C_{25}H_{39}N_2O_3Si$: 423.2730; Found: 429.2546.

J. N-(2-((tert-butyldimethylsilyl)ethynyl)cyclohexyl)picolinamide (3i)

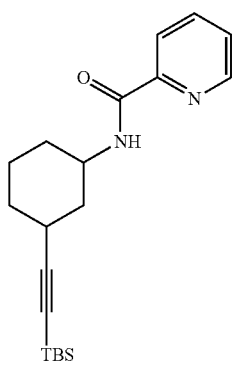

56 mg, 65% isolated yield. $R_f$=0.32 (hexane/EtOAc=9/1). Yellow liquid. $^1$H NMR (500 MHz, CHLOROFORM-d) δ ppm 8.53 (d, J=4.6 Hz, 1H), 8.19 (d, J=7.6 Hz, 1H), 7.95 (d, J=8.0 Hz, 1H), 7.84 (dt, J=1.5, 7.6 Hz, 1H), 7.41 (dd, J=5.0, 6.9 Hz, 1H), 4.02-3.83 (m, 1H), 2.52-2.40 (m, 1H), 2.34 (d, J=12.6 Hz, 1H), 2.09-1.94 (m, 2H), 1.88-1.78 (m, 1H), 1.44-1.21 (m, 4H), 0.90 (s, 10H), 0.06 (s, 6H). $^{13}$C NMR (126 MHz, CHLOROFORM-d) δ ppm 163.3, 150.0, 147.9, 137.3, 126.0, 122.2, 110.7, 81.9, 47.5, 39.1, 32.3, 32.2, 29.6, 26.0, 24.2, 16.4, -4.5. HRMS (EI): m/z Calcd for [M+H] $C_{20}H_{31}N_2OSi$: 343.2200; Found: 343.2200.

K. (3R)-tert-butyl 3-(picolinamido)-5-((triisopropylsilyl)ethynyl)piperidine-1-carboxylate (3j)

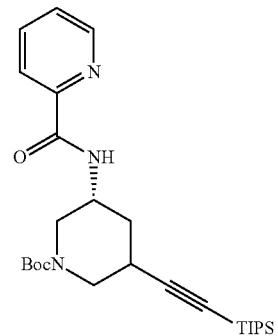

99 mg, 82% isolated yield. $R_f$=0.32 (hexane/EtOAc=7/3). Yellow liquid. $^1$H NMR (500 MHz, CHLOROFORM-d) δ ppm 8.53 (d, J=4.2 Hz, 1H), 8.19 (d, J=7.6 Hz, 1H), 7.96 (d, J=8.4 Hz, 1H), 7.85 (t, J=7.2 Hz, 1H), 7.56-7.36 (m, 1H), 4.30 (br. s., 2H), 4.15-3.91 (m, 1H), 2.75-2.59 (m, 2H), 2.45 (d, J=12.2 Hz, 1H), 1.52-1.43 (m, 9H), 1.13 (dd, J=5.0, 7.2 Hz, 2H), 1.09-0.93 (m, 21H). $^{13}$C NMR (126 MHz, CHLOROFORM-d) δ ppm 163.7, 154.3, 149.6, 147.9, 137.3, 126.3, 122.2, 107.7, 81.9, 80.3, 48.5, 48.0, 45.0, 37.7, 28.8, 28.3, 18.8, 18.8, 18.5, 12.5, 11.4, 11.0. HRMS (EI): m/z Calcd for [M+H]$C_{27}H_{43}N_3O_3Si$: 486.3152; Found: 486.3130.

L. N-(4-((triisopropylsilyl)ethynyl)heptan-2-yl)picolinamide (3k)

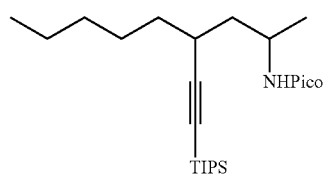

45 mg, 45% isolated yield. $R_f$=0.32 (hexane/EtOAc=9/1). Yellow liquid. $^1$H NMR (500 MHz, CHLOROFORM-d) δ ppm 8.54 (d, J=4.2 Hz, 1H), 8.21 (d, J=7.6 Hz, 1H), 7.91 (d, J=6.9 Hz, 1H), 7.87-7.78 (m, 1H), 7.42 (dd, J=5.3, 6.9 Hz, 1H), 4.48-4.25 (m, 1H), 2.59-2.48 (m, 1H), 1.92-1.84 (m, 1H), 1.84-1.77 (m, 1H), 1.77-1.65 (m, 1H), 1.61 (br. s., 2H), 1.50-1.41 (m, 3H), 1.38-1.29 (m, 4H), 1.13-1.02 (m, 23H), 0.94-0.90 (m, 4H). $^{13}$C NMR (126 MHz, CHLOROFORM-d) δ ppm 163.5, 150.3, 147.9, 137.3, 126.0, 122.2, 111.9, 81.4, 76.8, 44.5, 42.7, 37.6, 30.0, 21.1, 20.3, 18.6, 13.9, 11.3. HRMS (EI): m/z Calcd for [M+H] $C_{24}H_{41}N_2OSi$: 401.2988; Found: 401.2958.

M. N-(7-methyl-1-(triisopropylsilyl)oct-1-yn-4-yl)picolinamide (3l)

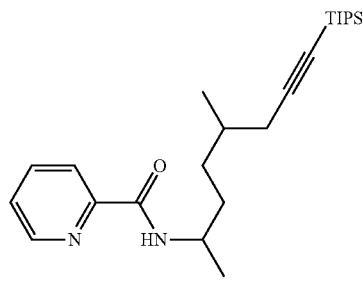

30 mg, 30% isolated yield. $R_f$=0.32 (hexane/EtOAc=9/1). Yellow liquid. $^1$H NMR (500 MHz, CHLOROFORM-d) δ ppm 8.46 (d, J=4.2 Hz, 2H), 8.19 (d, J=8.0 Hz, 1H), 7.82 (dt, J=1.5, 7.6 Hz, 1H), 7.39 (dt, J=1.0, 6.2 Hz, 1H), 4.19 (d, J=8.4 Hz, 1H), 2.52 (s, 1H), 2.45 (d, J=17.5 Hz, 2H), 2.03 (d, J=6.5 Hz, 2H), 1.65-1.55 (m, 2H), 1.41 (t, J=9.0 Hz, 1H), 1.32-1.21 (m, 1H), 1.19-0.95 (m, 25H). $^{13}$C NMR (126 MHz, CHLOROFORM-d) δ ppm 163.7, 150.3, 147.8, 137.0, 125.8, 122.3, 108.9, 84.2, 77.3, 76.7, 52.4, 48.3, 42.9, 40.3, 38.8, 28.1, 27.3, 18.6, 11.3 HRMS (EI): m/z Calcd for [M+H]$C_{24}H_{41}N_2OSi$: 401.2988 Found: 397.5653.

N. 6-methyl-N-(2-((triisopropylsilyl)ethynyl)cyclohexyl)picolinamide (3m)

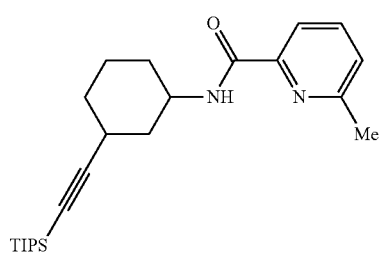

63 mg, 63% isolated yield. $R_f$=0.32 (hexane/EtOAc=9/1). Yellow liquid. $^1$H NMR (500 MHz, CHLOROFORM-d) δ ppm 8.08-7.93 (m, 2H), 7.73 (t, J=7.6 Hz, 1H), 7.29 (s, 1H), 3.95 (td, J=3.7, 12.1 Hz, 1H), 2.59 (s, 3H), 2.54-2.44 (m, 1H), 2.39 (d, J=12.6 Hz, 1H), 2.05 (t, J=13.0 Hz, 2H), 1.90-1.79 (m, 1H), 1.47-1.26 (m, 4H), 1.12-0.94 (m, 21H). $^{13}$C NMR (126 MHz, CHLOROFORM-d) δ ppm 163.5, 157.0, 149.3, 137.4, 125.7, 119.3, 112.1, 79.4, 47.6, 39.4, 32.6, 32.4, 29.8, 24.5, 24.2, 18.6, 11.2. HRMS (EI): m/z Calcd for [M+H] $C_{24}H_{39}N_2OSi$: 399.2826; Found: 399.2827.

O. 3-methyl-N-(2-((triisopropylsilyl)ethynyl)cyclohexyl)picolinamide (3n)

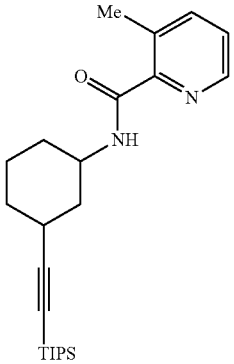

75 mg, 75% isolated yield. $R_f$=0.32 (hexane/EtOAc=9/1). Yellow liquid. $^1$H NMR (500 MHz, CHLOROFORM-d) δ ppm 8.37 (d, J=4.2 Hz, 1H), 8.03 (d, J=8.0 Hz, 1H), 7.57 (d, J=7.6 Hz, 1H), 7.29 (dd, J=4.6, 8.0 Hz, 1H), 3.97-3.80 (m, 1H), 2.74 (s, 3H), 2.52-2.42 (m, 1H), 2.36 (d, J=12.2 Hz, 1H), 2.02 (t, J=12.8 Hz, 2H), 1.83 (td, J=3.2, 13.4 Hz, 1H), 1.45-1.21 (m, 4H), 1.10-0.95 (m, 22H). $^{13}$C NMR (126 MHz, CHLOROFORM-d) δ ppm 165.1, 147.3, 145.3, 140.8, 135.4, 125.5, 112.2, 79.4, 47.4, 39.5, 32.6, 32.4, 29.8, 24.4, 20.5, 18.6, 11.2. HRMS (EI): m/z Calcd for [M+H] $C_{24}H_{39}N_2OSi$: 399.2826; Found: 399.2827.

P. N-(2-((triisopropylsilyl)ethynyl)cyclohexyl)pyrazine-2-carboxamide (3o)

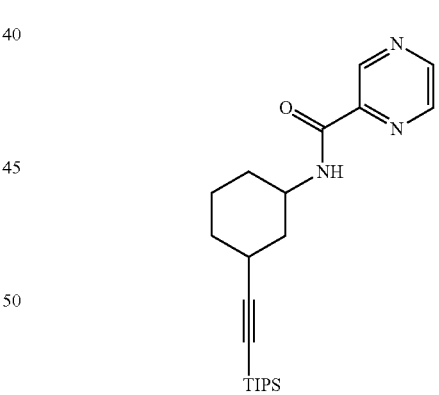

61 mg, 63% isolated yield. $R_f$=0.32 (hexane/EtOAc=8/2). Yellow liquid. $^1$H NMR (500 MHz, CHLOROFORM-d) δ ppm 9.42 (s, 1H), 8.76 (d, J=2.3 Hz, 1H), 8.53 (s, 1H), 7.71 (d, J=8.0 Hz, 1H), 3.99 (d, J=8.0 Hz, 1H), 2.57-2.47 (m, 1H), 2.38 (d, J=11.8 Hz, 1H), 2.10-2.02 (m, 3H), 1.87 (td, J=3.0, 13.4 Hz, 1H), 1.48-1.25 (m, 4H), 1.17-1.09 (m, 2H), 1.09-0.96 (m, 20H). $^{13}$C NMR (126 MHz, CHLOROFORM-d) δ ppm 162.0, 147.2, 144.5, 144.5, 142.4, 111.8, 79.7, 47.7, 39.2, 32.4, 32.2, 29.6, 24.2, 18.6, 11.2. HRMS (EI): m/z Calcd for [M+H] $C_{22}H_{36}N_3OSi$: 386.2622; Found: 386.2621.

Q. 5-methyl-N-(2-((triisopropylsilyl)ethynyl)cyclohexyl)pyrazine-2-carboxamide (3p)

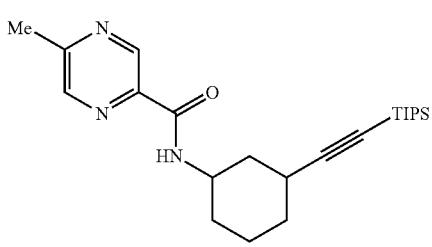

74 mg, 75% isolated yield. $R_f$=0.32 (hexane/EtOAc=8/2). Yellow liquid. $^1$H NMR (500 MHz, CHLOROFORM-d) δ ppm 9.26 (s, 1H), 8.36 (s, 1H), 7.63 (d, J=8.0 Hz, 1H), 4.05-3.86 (m, 1H), 2.65 (s, 3H), 2.53-2.41 (m, 1H), 2.36 (d, J=12.6 Hz, 1H), 2.07-1.97 (m, 2H), 1.89-1.79 (m, 1H), 1.46-1.29 (m, 3H), 1.29-1.22 (m, 1H), 1.11-0.92 (m, 22H). $^{13}$C NMR (126 MHz, CHLOROFORM-d) δ ppm 162.3, 156.9, 143.4, 142.1, 141.8, 111.9, 79.6, 47.6, 39.3, 32.4, 32.3, 29.7, 24.3, 21.8, 18.6, 11.2. HRMS (EI): m/z Calcd for [M+H] $C_{23}H_{38}N_3OSi$: 400.2779; Found: 400.2777.

R. N-(2-((triisopropylsilyl)ethynyl)cyclohexyl)quinoline-2-carboxamide (3q)

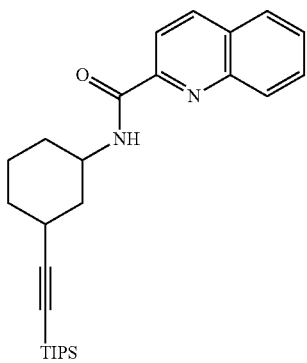

67 mg, 62% isolated yield. $R_f$=0.32 (hexane/EtOAc=9/1). Yellow liquid. $^1$H NMR (500 MHz, CHLOROFORM-d) δ ppm 8.35-8.21 (m, 2H), 8.20-8.04 (m, 2H), 7.87 (d, J=8.4 Hz, 1H), 7.76 (t, J=7.6 Hz, 1H), 7.67-7.53 (m, 1H), 4.08-3.92 (m, 1H), 2.57-2.48 (m, 1H), 2.43 (d, J=12.6 Hz, 1H), 2.15-1.99 (m, 2H), 1.93-1.82 (m, 1H), 1.53-1.29 (m, 4H), 1.14-0.94 (m, 21H). $^{13}$C NMR (126 MHz, CHLOROFORM-d) δ ppm 163.5, 149.9, 146.4, 137.4, 130.0, 129.6, 129.3, 127.8, 127.7, 118.9, 112.1, 79.5, 47.8, 39.5, 32.6, 32.4, 29.8, 24.5, 18.6, 11.2. HRMS (EI): m/z Calcd for [M−H] $C_{27}H_{37}N_2OSi$: 433.2670; Found: 433.2666.

S. N-(2-((triisopropylsilyl)ethynyl)cyclohexyl)isoquinoline-1-carboxamide (3r)

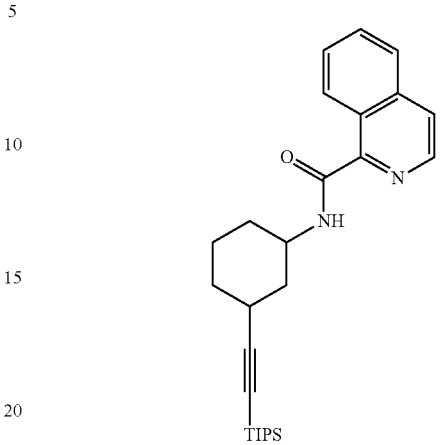

81 mg, 75% isolated yield. $R_f$=0.32 (hexane/EtOAc=9/1). Yellow liquid. $^1$H NMR (500 MHz, CHLOROFORM-d) δ ppm 9.60 (d, J=8.4 Hz, 1H), 8.45 (d, J=5.3 Hz, 1H), 8.12 (d, J=8.4 Hz, 1H), 7.84 (d, J=8.0 Hz, 1H), 7.79 (d, J=5.3 Hz, 1H), 7.75-7.64 (m, 2H), 4.08-3.92 (m, 1H), 2.60-2.48 (m, 1H), 2.44 (d, J=12.6 Hz, 1H), 2.10 (d, J=12.2 Hz, 1H), 2.03 (d, J=13.0 Hz, 1H), 1.87 (td, J=3.1, 13.5 Hz, 1H), 1.50-1.26 (m, 4H), 1.08-0.93 (m, 21H). $^{13}$C NMR (126 MHz, CHLOROFORM-d) δ ppm 165.2, 148.4, 140.1, 137.4, 130.4, 128.6, 127.9, 127.0, 126.7, 124.2, 112.1, 79.5, 47.7, 39.4, 32.6, 32.3, 29.8, 24.4, 18.6, 11.2. HRMS (EI): m/z Calcd for [M−H] $C_{27}H_{37}N_2OSi$: 433.2670; Found: 433.2666.

T. 1-methyl-N-(2-((triisopropylsilyl)ethynyl)cyclohexyl)-1H-indazole-3-carboxamide (3s)

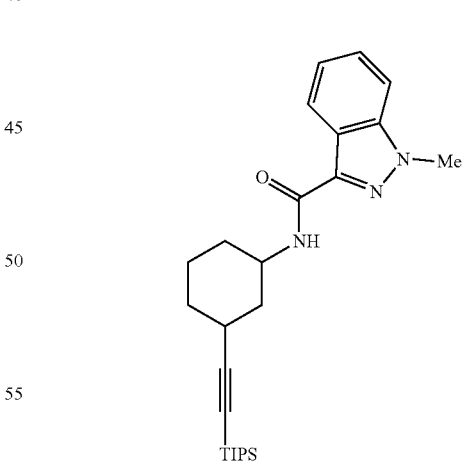

49 mg, 45% isolated yield. $R_f$=0.32 (hexane/EtOAc=9/1). Yellow liquid. $^1$H NMR (500 MHz, CHLOROFORM-d) δ ppm 8.38 (d, J=8.4 Hz, 1H), 7.48-7.37 (m, 2H), 7.29 (d, J=7.2 Hz, 1H), 6.88 (d, J=8.4 Hz, 1H), 4.09 (s, 3H), 4.05-3.93 (m, 1H), 2.58-2.46 (m, 1H), 2.42 (d, J=12.6 Hz, 1H), 2.14-1.97 (m, 2H), 1.90-1.77 (m, 1H), 1.47-1.24 (m, 4H), 1.10-0.94 (m, 22H). $^{13}$C NMR (126 MHz, CHLOROFORM-d) δ ppm 161.7, 141.2, 137.3, 126.8, 122.9, 122.8, 122.5, 112.2, 109.0, 79.4, 47.2, 39.6, 35.9, 32.5, 29.8, 24.4, 18.6, 11.2. HRMS (EI): m/z Calcd for [M+H] $C_{26}H_{40}N_3OSi$: 438.2935; Found: 438.2935.

U. 1-(2,4-dichlorophenyl)-4-methyl-5-phenyl-N-(2-((triisopropylsilyl)ethynyl) cyclohexyl)-1H-pyrazole-3-carboxamide (3t)

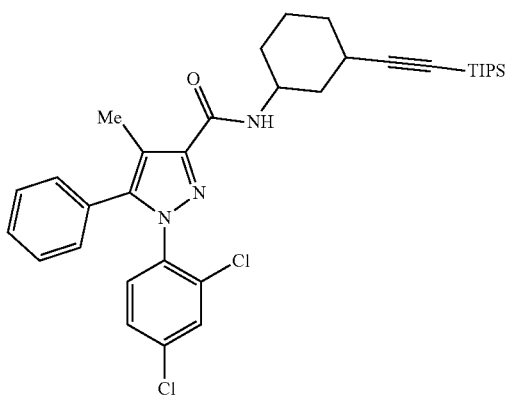

83 mg, 55% isolated yield. $R_f$=0.32 (hexane/EtOAc=8/2). Yellow liquid. $^1$H NMR (500 MHz, CHLOROFORM-d) δ ppm 7.21-7.10 (m, 7H), 7.04-6.93 (m, 2H), 6.68 (d, J=8.0 Hz, 1H), 3.87-3.71 (m, 1H), 2.37-2.30 (m, 1H), 2.26-2.18 (m, 4H), 1.95-1.81 (m, 2H), 1.71-1.63 (m, 1H), 1.29-1.22 (m, 1H), 1.21-1.03 (m, 5H), 0.96-0.89 (m, 22H). $^{13}$C NMR (126 MHz, CHLOROFORM-d) δ ppm 162.0, 144.9, 144.2, 136.2, 135.7, 133.1, 130.6, 130.2, 129.6, 128.8, 128.6, 128.5, 127.7, 117.6, 112.2, 79.4, 47.3, 39.6, 32.5, 32.4, 29.8, 24.5, 18.6, 18.5, 11.3, 11.2, 9.5. HRMS (EI): m/z Calcd for [M+H] $C_{34}H_{44}ON_3Cl_2Si$: 608.2625; Found: 608.2623.

V. 2-((triisopropylsilyl)ethynyl)cyclohexanamine (4a)

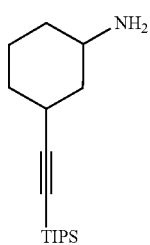

$^1$H NMR (500 MHz, CHLOROFORM-d) δ ppm 5.00 (brs., 3H), 2.97 (br. s., 1H), 2.33 (d, J=12.2 Hz, 1H), 2.05 (d, J=6.1 Hz, 1H), 1.96 (brs., 2H), 1.82 (brs., 1H), 1.38-1.26 (m, 4H), 1.06-1.02 (m, 21H). $^{13}$C NMR (126 MHz, CHLOROFORM-d) δ ppm 111.1, 80.2, 49.7, 38.1, 32.1, 31.2, 29.4, 23.8, 18.6, 11.2. HRMS (EI): m/z Calcd for [M+H] $C_{17}H_{34}Si$: 280.2455; Found: 280.2457.

W. (E)-ethyl 2-(7-oxo-6-(2-((triisopropylsilyl)ethynyl)cyclohexyl)-6,7-dihydro-5H-pyrrolo[3,4-b]pyridin-5-ylidene)acetate (4b)

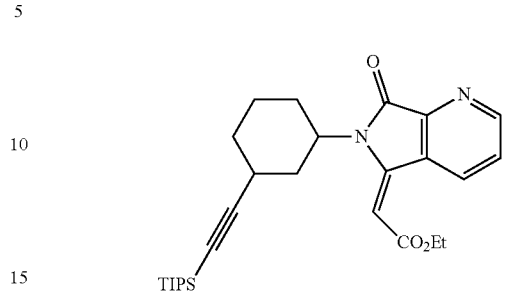

$^1$H NMR (500 MHz, CHLOROFORM-d) δ ppm 9.34 (dd, J=1.0, 8.2 Hz, 1H), 8.82 (d, J=3.8 Hz, 1H), 7.53 (dd, J=4.8, 8.2 Hz, 1H), 5.96 (brs., 1H), 4.31 (q, J=7.0 Hz, 2H), 2.48 (d, J=9.5 Hz, 3H), 2.14-1.98 (m, 2H), 1.98-1.87 (m, 1H), 1.78 (d, J=12.6 Hz, 1H), 1.56-1.33 (m, 6H), 1.08-0.98 (m, 22H). $^{13}$C NMR (126 MHz, CHLOROFORM-d) δ ppm 165.8, 165.0, 152.8, 148.3, 135.9, 128.7, 126.4, 111.2, 80.2, 60.9, 35.6, 32.1, 30.9, 28.4, 25.3, 18.6, 18.3, 14.3, 11.2. HRMS (EI): m/z Calcd for [M+H] $C_{28}H_{41}N_2O_3Si$: 481.2881; Found: 481.2875.

X. N-(2-ethynylcyclohexyl)picolinamide (4c)

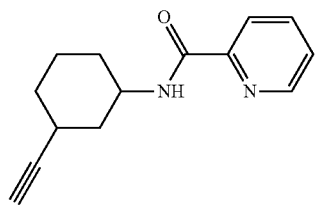 [SMILES: C#CC1CCCC(NC(=O)c2ccccn2)C1]

$^1$H NMR (500 MHz, CHLOROFORM-d) δ ppm 8.53 (d, J=4.2 Hz, 1H), 8.19 (d, J=7.6 Hz, 1H), 8.11-7.89 (m, 1H), 7.83 (dt, J=1.5, 7.6 Hz, 1H), 7.45-7.30 (m, 1H), 4.03-3.88 (m, 1H), 2.52-2.37 (m, 1H), 2.32 (d, J=12.6 Hz, 1H), 2.11-1.93 (m, 3H), 1.93-1.75 (m, 1H), 1.48-1.24 (m, 4H). $^{13}$C NMR (126 MHz, CHLOROFORM-d) δ ppm 163.3, 150.0, 147.9, 137.3, 126.0, 122.2, 87.5, 68.1, 47.3, 38.7, 32.2, 32.0, 28.2, 23.9. HRMS (EI): m/z Calcd for [M+H] $C_{14}H_{17}N_2O$: 229.1335; Found: 229.1335.

Y. N-(2-(1-(3-methylbenzyl)-1H-1,2,3-triazol-4-yl)cyclohexyl)picolinamide (4d)

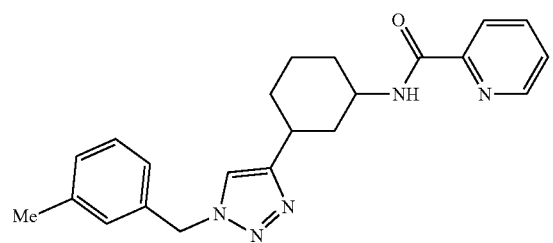 [SMILES: Cc1cccc(Cn2cc(C3CCCC(NC(=O)c4ccccn4)C3)nn2)c1]

$^1$H NMR (500 MHz, CHLOROFORM-d) δ ppm 8.51 (d, J=4.6 Hz, 1H), 8.18 (d, J=8.0 Hz, 1H), 7.95 (d, J=8.0 Hz, 1H), 7.82 (t, J=7.6 Hz, 1H), 7.40 (dd, J=5.3, 6.9 Hz, 1H), 7.27-7.21 (m, 1H), 7.19-7.10 (m, 2H), 7.10-7.00 (m, 2H), 5.43 (s, 2H), 4.07 (dt, J=3.8, 7.8 Hz, 1H), 2.98-2.77 (m, 1H), 2.41 (d, J=12.2 Hz, 1H), 2.33 (s, 3H), 2.18-2.05 (m, 2H), 2.03-1.88 (m, 2H), 1.61-1.51 (m, 1H), 1.47-1.37 (m, 2H), 1.36-1.27 (m, 1H). $^{13}$C NMR (126 MHz, CHLOROFORM-d) δ ppm 163.3, 152.5, 150.0, 147.9, 138.8, 137.3, 134.7, 129.3, 128.9, 128.7, 126.0, 125.1, 122.1, 119.3, 54.0, 48.2, 38.9, 34.3, 32.5, 32.0, 24.6, 21.3. HRMS (EI): m/z Calcd for [M+H] $C_{22}H_{26}N_2O$: 376.2132; Found: 376.2130.

Z. N-(2-(p-tolylethynyl)cyclohexyl)picolinamide (4e)

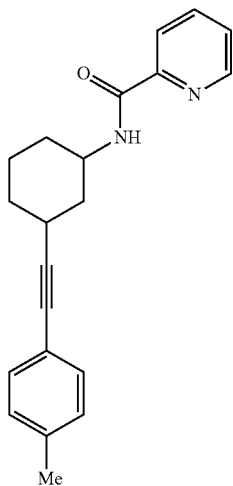 [SMILES: Cc1ccc(C#CC2CCCC(NC(=O)c3ccccn3)C2)cc1]

$^1$H NMR (500 MHz, CHLOROFORM-d) δ ppm 8.45 (d, J=4.2 Hz, 1H), 8.20 (d, J=7.6 Hz, 1H), 8.15-8.03 (m, 1H), 7.83 (dt, J=1.5, 7.6 Hz, 1H), 7.47-7.32 (m, 1H), 7.32-7.21 (m, 2H), 7.08 (d, J=8.0 Hz, 2H), 4.13-3.95 (m, 1H), 2.78-2.62 (m, 1H), 2.42-2.28 (m, 4H), 2.07-1.96 (m, 2H), 1.90 (dd, J=3.8, 9.9 Hz, 1H), 1.59-1.42 (m, 3H), 1.42-1.30 (m, 1H). $^{13}$C NMR (126 MHz, CHLOROFORM-d) δ ppm 163.4, 150.0, 147.9, 137.5, 137.2, 131.4, 128.9, 126.0, 122.2, 120.7, 92.2, 77.3, 76.7, 47.3, 38.7, 32.2, 32.1, 28.9, 23.7, 21.4. HRMS (EI): m/z Calcd for [M+H] $C_{21}H_{23}N_2O$: 319.1805; Found: 319.1805.

ADVANTAGES OF THE INVENTION

1. The developed alkynylation strategy is simple, efficient, and tolerant of various ring size including five to eight member cyclic, quaternary amines, and N-heterocyclic motifs.
2. The reaction can be scaled up under mild conditions.

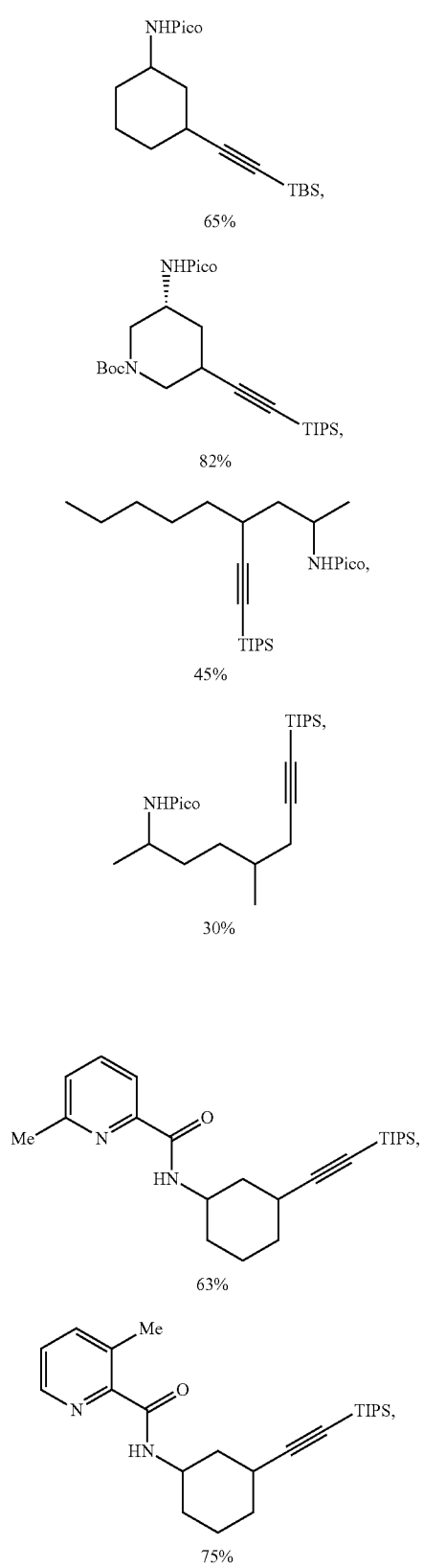
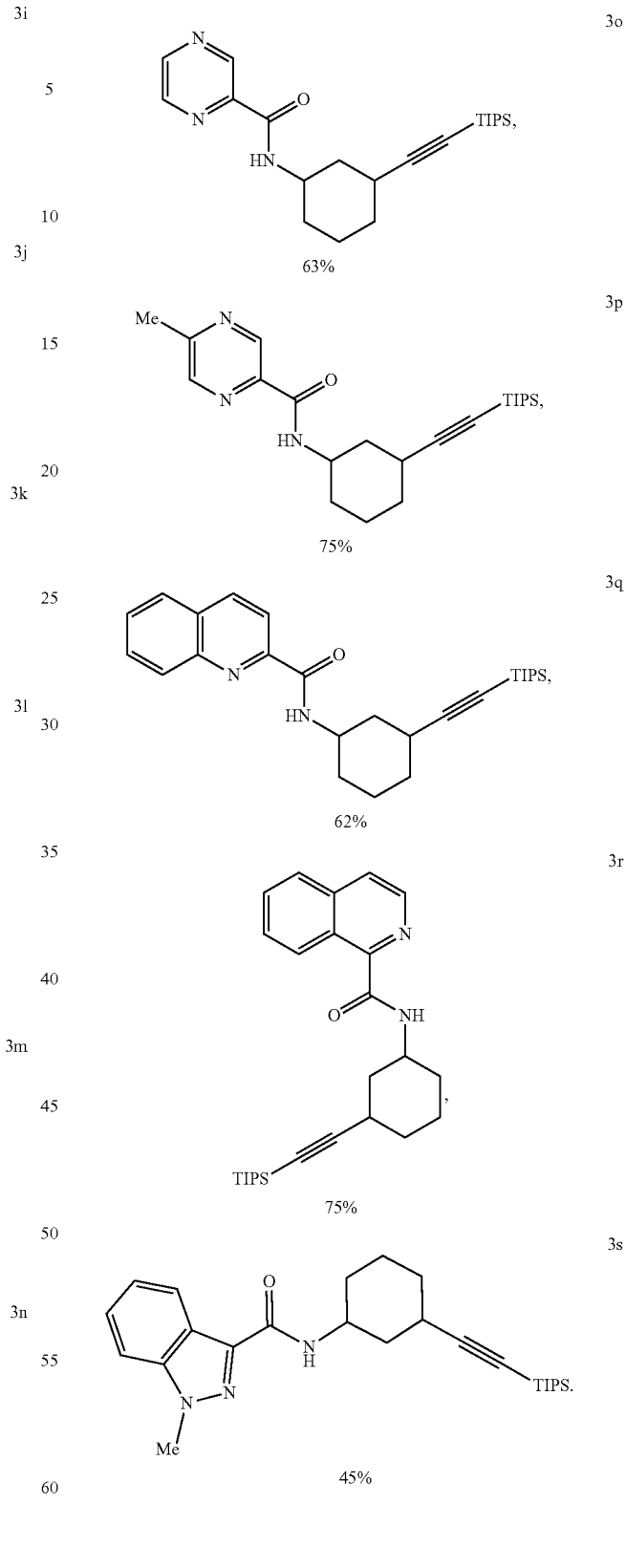

The invention claimed is:
1. A process for Palladium (II)-catalyzed γ C(sp$^3$)-H alkynylation of amines using picolinamide as directing group comprises heating the reaction mixture of amide, haloalkyne, palladium catalyst, oxidant and solvent for a time period in the range of 18 to 20 hours at temperature in the range of 130° C. to 140° C. to afford alkynylated product; wherein said reaction is represented as below

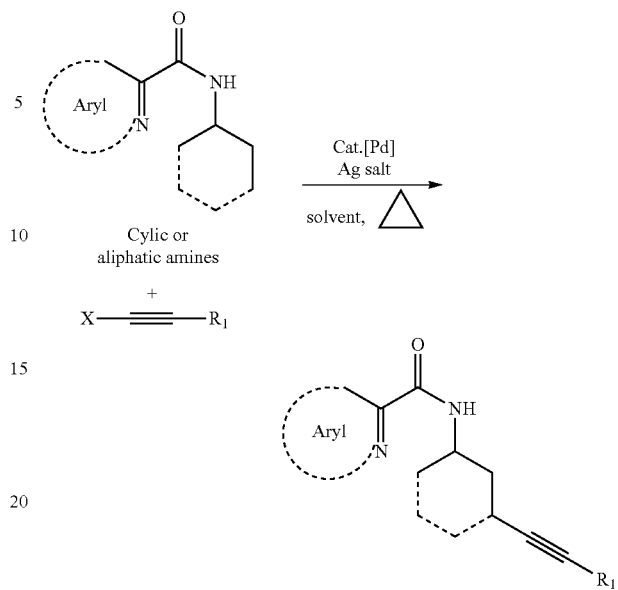

Wherein X—C≡C—R$_1$ is a haloalkyne where X is a halogen and R$_1$ is selected from the group consisting of triisopropylsilyl, t-butyl dimethyl silyl triphenyl silyl, and phenyl dimethylsilyl.

2. The process as claimed in claim 1, wherein said amide is selected from the group consisting of N-cyclohexylpicolinamide, N-(4-methylcyclohexyl)picolinamide, N-(4-butyl-cyclohexyl)picolinamide, N-cyclopentylpicolinamide, N-cycloheptylpicolinamide, N-cyclooctylpicolinamide methyl 1-(picolinamido)cyclopentanecarboxylate, ethyl 1-(picolinamido)cyclopentanecarboxylate, tert-butyl 3-(picolinamido)piperidine-1-carboxylate, N-(5-methylhexan-2-yl)picolinamide, N-(octan-2-yl)picolinamide, N-cyclohexyl-6-methylpicolinamide, N-cyclohexyl-3-methylpicolinamide, N-cyclohexylpyrazine-2-carboxamide, N-cyclohexyl-5-methylpyrazine-2-carboxamide, N-cyclohexylquinoline-2-carboxamide, N-cyclohexylisoquinoline-1-carboxamide, and N-cyclohexyl-1-methyl-1H-indazole-3-carboxamide.

3. The process as claimed in claim 1, wherein said amine is selected from the group consisting of Cyclohexanamine, 4-methylcyclohexanamine, 4-butylcyclohexanamine, cyclopentanamine, cycloheptanamine, cyclooctanamine, methyl 1-aminocyclopentanecarboxylate, ethyl 1-aminocyclopentanecarboxylate, 5-methylhexan-2-amine, and nonan-2-amine.

4. The process as claimed in claim 1, wherein said haloalkyne is selected from the group consisting of (bromoethynyl)triisopropylsilane, (bromoethynyl)dimethyl(phenyl)silane, (bromoethynyl)(tert-butyl)dimethyl silane, (bromoethynyl)(ethyl)dimethylsilane, tert-butyl(iodoethynyl)dimethylsilane, and (bromoethynyl)triphenylsilane.

5. The process as claimed in claim 1, wherein said solvent is selected from the group consisting of toluene, trifluorotoluene, decane, octane, mesitylene, dioxane, t-amyl alcohol, dicholoro methane, and dicholoro ethane.

6. The process as claimed in claim 1, wherein said palladium catalyst is selected from the group consisting of Pd(OAc)$_2$, Pd(OPiv)$_2$, Pd(PPh$_3$)$_4$, Pd(PPh$_3$)$_2$Cl$_2$, Pd(dba)$_4$, Pd(OTf)$_2$, Pd(CH$_3$CN)$_4$BF$_4$, PdCl$_2$, and Pd(TFA)$_2$.

7. The process as claimed in claim 1, wherein said oxidant is selected from the group consisting of silver carbonate, silver acetate, silver benzoate, silver triflate, and silver nitrate.

8. The process as claimed in claim 1, wherein said alkynylated product is selected from the group consisting of
N-(2-((triisopropylsilyl)ethynyl)cyclohexyl)picolinamide (3a);
N-(4-methyl-2-((triisopropylsilyl)ethynyl)cyclohexyl)picolinamide (3b);
N-(4-butyl-2-((triisopropylsilyl)ethynyl)cyclohexyl)picolinamide (3c);
N-(2-((triisopropylsilyl)ethynyl)cyclopentyl)picolinamide (3d);
N-(2-((triisopropylsilyl)ethynyl)cycloheptyl)picolinamide (3e);
N-(2-((triisopropylsilyl)ethynyl)cyclooctyl)picolinamide (3f);
Methyl 1-(picolinamido)-3-((triisopropylsilyl)ethynyl)cyclopentanecarboxylate (3g);
Ethyl 1-(picolinamido)-3-((triisopropylsilyl)ethynyl)cyclopentanecarboxylate (3h);
N-(2-((tert-butyldimethylsilyl)ethynyl)cyclohexyl)picolinamide (3i);
(3R)-tert-butyl 3-(picolinamido)-5-((triisopropylsilyl)ethynyl)piperidine-1-carboxylate (3j);
N-(4-((triisopropylsilyl)ethynyl)heptan-2-yl)picolinamide (3k);
N-(7-methyl-1-(triisopropylsilyl)oct-1-yn-4-yl)picolinamide (3l);
6-methyl-N-(2-((triisopropylsilyl)ethynyl)cyclohexyl)picolinamide (3m);
3-methyl-N-(2-((triisopropylsilyl)ethynyl)cyclohexyl)picolinamide (3n);
N-(2-((triisopropylsilyl)ethynyl)cyclohexyl)pyrazine-2-carboxamide (3o);
5-methyl-N-(2-((triisopropylsilyl)ethynyl)cyclohexyl)pyrazine-2-carboxamide (3p);
N-(2-((triisopropylsilyl)ethynyl)cyclohexyl)quinoline-2-carboxamide (3q);
N-(2-((triisopropylsilyl)ethynyl)cyclohexyl)isoquinoline-1-carboxamide (3r), and
1-methyl-N-(2-((triisopropylsilyl)ethynyl)cyclohexyl)-1H-indazole-3-carboxamide (3s)

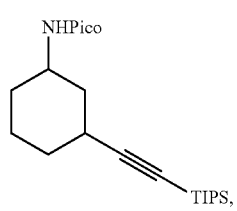

3a

85%

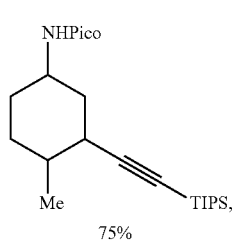

3b

75%

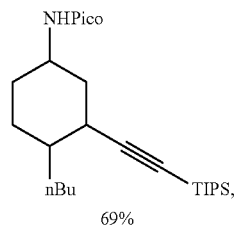

3c

69%

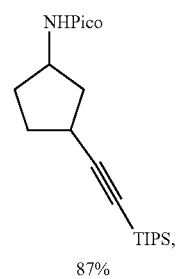

3d

87%

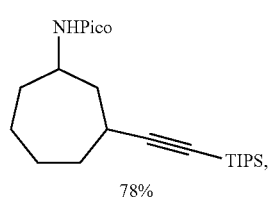

3e

78%

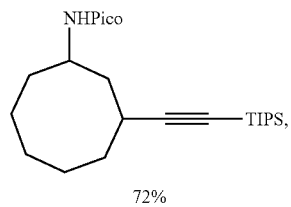

3f

72%

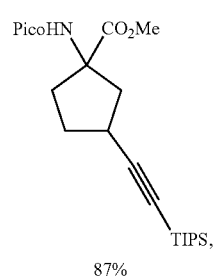

3g

87%

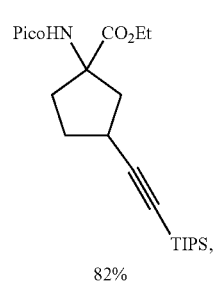

3h

82%